(12) United States Patent
Prodoehl et al.

(10) Patent No.: US 10,279,070 B2
(45) Date of Patent: May 7, 2019

(54) BELT WITH TREATED INNER SURFACE

(71) Applicant: The Procter & Gamble Company, Cincinnati, OH (US)

(72) Inventors: Ellyne Elizabeth Prodoehl, West Chester, OH (US); Ronald Joseph Zink, Blue Ash, OH (US); Koichi Morimoto, Beijing (CN); Albert Choy So, Beijing (CN); Chunmin Cheng, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 14/726,812

(22) Filed: Jun. 1, 2015

(65) Prior Publication Data

US 2016/0317695 A1    Nov. 3, 2016

(30) Foreign Application Priority Data

Apr. 29, 2015 (WO) ................. PCT/CN2015/077760

(51) Int. Cl.
| | | |
|---|---|---|
| *A61F 13/49* | (2006.01) | |
| *A61F 13/84* | (2006.01) | |
| *A61L 15/40* | (2006.01) | |
| *A61L 15/32* | (2006.01) | |
| *A61L 15/20* | (2006.01) | |
| *A61L 15/48* | (2006.01) | |
| *A61F 13/51* | (2006.01) | |
| *A61F 13/511* | (2006.01) | |

(52) U.S. Cl.
CPC ......... *A61L 15/40* (2013.01); *A61F 13/49011* (2013.01); *A61F 13/8405* (2013.01); *A61L 15/20* (2013.01); *A61L 15/32* (2013.01); *A61L 15/48* (2013.01); *A61F 13/49061* (2013.01); *A61F 2013/51059* (2013.01); *A61F 2013/51117* (2013.01)

(58) Field of Classification Search
CPC .......... A61F 13/49011; A61F 13/49012; A61F 13/49061; A61F 13/51113; A61F 13/51405; A61F 13/64; A61F 13/8405; A61F 2013/49023; A61F 2013/51059; A61F 2013/51061; A61F 2013/51064; A61F 2013/51066; A61F 2013/51069; A61F 2013/51071; A61F 2013/51073; A61F 2013/51076; A61F 2013/51117; A61F 2013/8455; A61F 2013/8458; A61F 2013/8461; A61F 2013/8467; A61F 2013/49088; A61F 2013/4909; A61F 2013/49095
See application file for complete search history.

(56) References Cited

U.S. PATENT DOCUMENTS

| | | |
|---|---|---|
| 3,848,594 A | 11/1974 | Buell |
| 4,662,875 A | 5/1987 | Hirotsu et al. |
| 4,699,622 A | 10/1987 | Toussant et al. |
| 4,778,458 A * | 10/1988 | Gronostajski ......... A61F 5/4401 427/394 |
| 4,846,815 A | 7/1989 | Scripps |

(Continued)

*Primary Examiner* — Lynne Anderson
(74) *Attorney, Agent, or Firm* — James T. Fondriest; Kathleen Y. Carter

(57) ABSTRACT

An absorbent article having a belt structure, wherein the inner surface of the belt comprises a treatment and wherein the inner surface of the belt is different than the outer surface of the belt.

17 Claims, 6 Drawing Sheets

(56) References Cited

U.S. PATENT DOCUMENTS

| | | | |
|---|---|---|---|
| 4,894,060 A | 1/1990 | Nestegard | |
| 4,946,527 A | 8/1990 | Battrell | |
| 5,143,679 A | 9/1992 | Weber et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 5,635,191 A | 6/1997 | Roe et al. | |
| 6,166,285 A * | 12/2000 | Schulte | A61F 13/494 424/402 |
| 6,428,526 B1 | 8/2002 | Heindel et al. | |
| 6,432,098 B1 | 8/2002 | Kline et al. | |
| 6,447,497 B1 | 9/2002 | Olson | |
| 6,545,197 B1 | 4/2003 | Muller et al. | |
| 6,626,879 B1 | 9/2003 | Ashton et al. | |
| 6,626,897 B2 | 9/2003 | Ahston et al. | |
| 6,911,024 B2 * | 6/2005 | Kusibojoska | A61F 13/64 604/386 |
| 7,056,411 B2 | 6/2006 | Desai et al. | |
| 7,781,641 B2 * | 8/2010 | Kasai | A61F 13/8405 604/360 |
| 7,833,211 B2 | 11/2010 | Mansfield et al. | |
| 8,062,454 B2 | 11/2011 | Yamamoto et al. | |
| 8,075,722 B2 | 12/2011 | Yakahashi et al. | |
| 8,171,972 B2 | 5/2012 | Eckstein et al. | |
| 8,177,766 B2 | 5/2012 | Mansfield | |
| 8,182,627 B2 | 5/2012 | Eckstein et al. | |
| 8,193,407 B2 | 6/2012 | Mansfield et al. | |
| 8,283,515 B2 * | 10/2012 | Lagerstedt-Eidrup | A61F 13/8405 424/76.5 |
| 8,395,012 B2 * | 3/2013 | Bacon | A61F 13/51 514/938 |
| 2003/0091807 A1 | 5/2003 | Desai et al. | |
| 2004/0222553 A1 | 11/2004 | Desai et al. | |
| 2005/0222546 A1 | 10/2005 | Vargo et al. | |
| 2008/0287899 A1 * | 11/2008 | Morrell-Schwartz | A61F 13/15699 604/365 |
| 2009/0069772 A1 | 3/2009 | Sauer et al. | |
| 2009/0069773 A1 | 3/2009 | Sauer et al. | |
| 2009/0069774 A1 | 3/2009 | Sauer et al. | |
| 2009/0069775 A1 | 3/2009 | Sauer et al. | |
| 2009/0069777 A1 | 3/2009 | Sauer et al. | |
| 2009/0069778 A1 | 3/2009 | Sauer et al. | |
| 2009/0069779 A1 | 3/2009 | Sauer et al. | |
| 2009/0069781 A1 | 3/2009 | Sauer et al. | |
| 2009/0069782 A1 | 3/2009 | Sauer et al. | |
| 2010/0193135 A1 | 8/2010 | Eckstein et al. | |
| 2011/0319853 A1 * | 12/2011 | Yamashita | A61F 13/49011 604/385.3 |
| 2012/0022485 A1 | 1/2012 | Roe et al. | |
| 2012/0157955 A1 | 6/2012 | Ashton et al. | |
| 2012/0193138 A1 | 8/2012 | Jones | |
| 2012/0271265 A1 | 10/2012 | Eckstein et al. | |
| 2012/0277713 A1 | 11/2012 | Raycheck et al. | |
| 2013/0211363 A1 | 8/2013 | Lavon et al. | |
| 2013/0270067 A1 | 10/2013 | Papsdorf et al. | |
| 2013/0306226 A1 | 11/2013 | Zink et al. | |
| 2013/0310793 A1 | 11/2013 | Wade et al. | |
| 2013/0310796 A1 | 11/2013 | Zink et al. | |
| 2013/0324956 A1 | 12/2013 | Zink et al. | |
| 2014/0088538 A1 * | 3/2014 | Borrero | A61F 13/49011 604/385.16 |
| 2014/0163509 A1 * | 6/2014 | Gassner | A61F 13/49061 604/385.16 |
| 2015/0083310 A1 | 3/2015 | Wade et al. | |
| 2015/0088088 A1 | 3/2015 | Wade et al. | |

* cited by examiner

BELT WITH TREATED INNER SURFACE

FIELD

The present disclosure generally relates to pull-on disposable absorbent articles comprising an elastomeric belt wherein the inner surface of the belt comprises a treatment.

BACKGROUND OF THE INVENTION

Infants and other incontinent individuals wear disposable absorbent articles such as diapers to receive and contain urine and other body exudates. Training pants or pull-on diapers have become popular for use on children able to walk and often who are toilet training. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled at least in part with elasticized bands of rubber or other materials positioned along the periphery of the respective opening.

While a stretchable waist opening generating high contraction force may assist in anchoring the waist-opening of the pull-on article to the wearer's body, such high contraction force sometimes causes not only difficulty for a caregiver to apply and remove the absorbent article, but may also cause marks on the skin of the wearer or be an irritation to the wearer. There is a need for articles where in the waist area the inner surface may be different than the outer surface. The inner surface, which touches the wearer's skin, may be the same material as the outer surface or other layers in the waist, but it may be treated with additional materials, such as lotions or surfactants, that can soothe or ease the friction of the force holding the article on. Or the inner surface may be treated, such as through aperturing or texturing, such that the inner surface connotes and/or delivers a softer feeling. Or the inner surface may be a completely different material than other parts of the waist, a material that has a higher coefficient of friction to help the article stay in place, or that has a higher basis weight. Thus, there is a continuing need for a waist inner material that has specific properties that benefit contact with the wearer's skin. Further, there is a continuing need for providing such properties that benefit contact with the wearer's skin in without significant cost added to the product. Further, there is a continuing need for providing such treatment on-line in the production process.

SUMMARY

An absorbent article having a front waist region, a rear waist region, and a crotch region, and comprising a central chassis occupying the crotch region and comprising left and right longitudinal edges; a liquid permeable topsheet; a backsheet, and an absorbent core disposed between the topsheet and the backsheet; a belt structure disposed about the central chassis, the belt structure comprising an elasticized multilayer web overlaying the backsheet to the outside thereof in the front and rear waist regions, the belt structure extending laterally and longitudinally outward from the chassis and laterally from each of the left and right longitudinal edges in each of the front and rear waist regions, the belt structure having a front portion having a front waist edge, front left and right leg opening edges, and front left and right side edges, and the belt structure having a rear portion having a rear waist edge, rear left and right leg opening edges, and rear left and right side edges, the respective front and rear left side edges and the respective front and rear right side edges being joined at side seams, the belt structure forming a waist opening and left and right leg openings, wherein each of the front and rear portions of the belt structure further comprises: an inner layer formed of an inner nonwoven web comprising an inner surface; an outer layer formed of an outer nonwoven web comprising an outer surface; wherein the inner surface of the belt comprises a treatment and wherein the inner surface is different than the outer surface.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION

Figure 1:
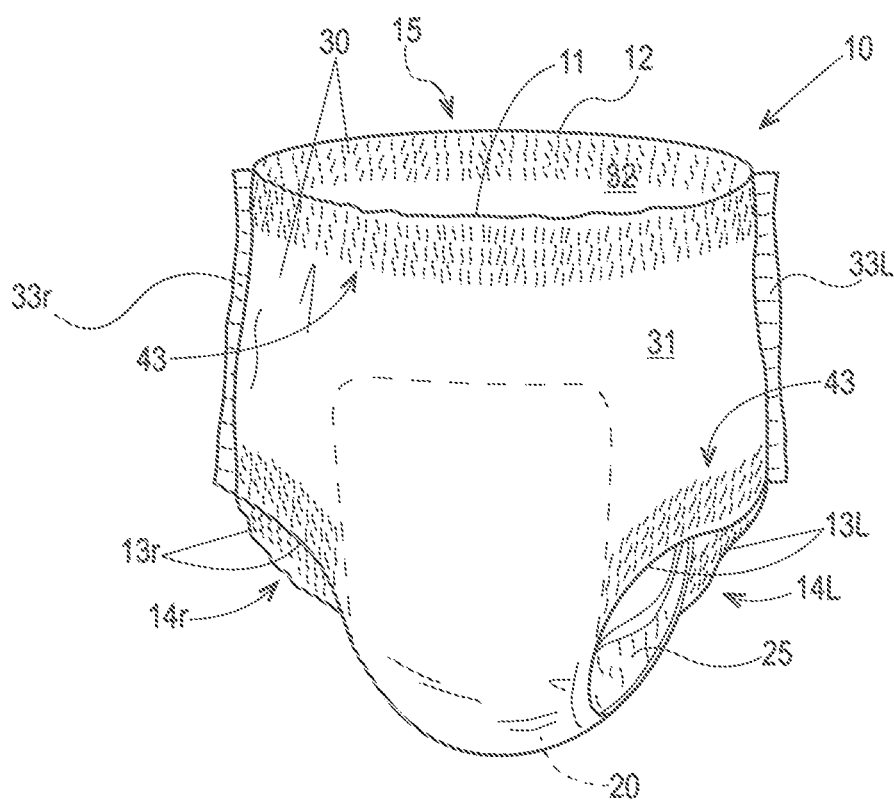
FIG. 1 is simplified perspective view of a disposable absorbent pant.

Various non-limiting embodiments of the present disclosure will now be described to provide an overall understanding of the principles of the structure, function, manufacture, and use of the absorbent articles disclosed herein. One or more examples of these non-limiting embodiments are illustrated in the accompanying drawings. Those of ordinary skill in the art will understand that the absorbent articles described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

The following term explanations may be useful in understanding the present disclosure:

"Absorbent article" refers to pull-on garments generally worn by infants and other incontinent individuals to absorb and contain urine, feces and/or menses. It should be understood, however, that the term absorbent article is also applicable to other garments such as training pants, incontinent briefs, feminine hygiene garments or panties, and the like. In some embodiments, "absorbent article" may refer to a taped diaper.

The terms "elastic," "elastomer," and "elastomeric" refer to a material which generally is able to extend to a strain of at least 50% without breaking or rupturing, and is able to recover substantially to its original dimensions after the deforming force has been removed.

"Lateral", with respect to a pant and its wearer, refers to the direction generally perpendicular with the wearer's standing height, or the horizontal direction when the wearer is standing. "Lateral" is also the direction generally perpendicular to a line extending from the midpoint of the front waist edge to the midpoint of the rear waist edge.

"Longitudinal", with respect to a pant and its wearer, refers to the direction generally parallel with the wearer's standing height, or the vertical direction when the wearer is standing. "Longitudinal" is also the direction generally parallel to a line extending from the midpoint of the front waist edge to the midpoint of the rear waist edge.

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the absorbent article is the disposable absorbent pull-on garment, shown in FIG. 1.

The term "substrate" is used herein to describe a material that is primarily two-dimensional (i.e., in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, and films and foils, such as polymeric films or metallic foils, for example. These materials may be used alone or may comprise two or more layers laminated together. As such, a web may be a substrate or may be a laminate of two or more substrates.

Article

Articles in the present disclosure provide a waist with an inner surface that has been treated. Many existing absorbent pants are structured such that a backsheet and topsheet of a central chassis structure extend to, and from, the front and rear waist edges of the pant in the regions near the wearer's navel in the front, and small of the back in the rear. Separate and discrete side/hip panels are joined to longitudinal (side) edges of the central chassis structure in its front and rear regions, joining them to form the pant structure.

An alternate configuration for absorbent pants is one in which the central chassis structure does not extend to, or form, the front and rear waist edges of the pant. Rather, an elasticized belt structure entirely encircles the wearer's waist and forms the waist edge about the entire pant, and the side/hip panels. The central chassis is joined to the belt structure, usually on the inside thereof, with its ends disposed at locations in the front and rear waist regions somewhat below the waist edges of the belt structure. The elastic belt is usually relatively wide (in the longitudinal direction) and elastically stretchable in the lateral direction. It entirely encircles the wearer's waist, and thereby covers a relatively large amount of the wearer's skin. This configuration is sometimes known as a "belt" or "balloon" configuration (hereinafter, "belt" configuration).

FIG. 1 is a general simplified perspective depiction of a disposable absorbent pant 10 having a belt configuration. Pant 10 may include a central chassis 20 and a belt structure 30. Belt structure 30 may be elastically extensible in the lateral direction, providing elastic stretchability for ease of donning, and a snug and comfortable fit following donning Central chassis 20 may include a wearer-facing, liquid permeable topsheet (not specifically shown in FIG. 1), an outer- or garment-facing backsheet (not specifically shown in FIG. 1) and an absorbent core (not specifically shown in FIG. 1) sandwiched or enveloped between the topsheet and backsheet. A pair of laterally opposing, longitudinally extending barrier cuffs 25 also may be included with the central chassis in a crotch region thereof, disposed adjacent to the topsheet. Generally the central chassis and barrier cuffs may have any construction and components, including leg cuff structures, suitable for disposable diapers, training pants, and adult incontinence pants, such as, but not limited to, those described in U.S. Pat. No. 8,939,957 and application(s) claiming priority thereto. Belt structure 30 may have a front portion 31 and a rear portion 32. Front and rear portions 31, 32 may be joined together at respective left and right side seams 33l, 33r. Belt structure 30 may form front and rear waist edges 11, 12 defining waist opening 15, and at least portions of left and right leg opening edges 13l, 13r of the pant 10.

Figure 2:
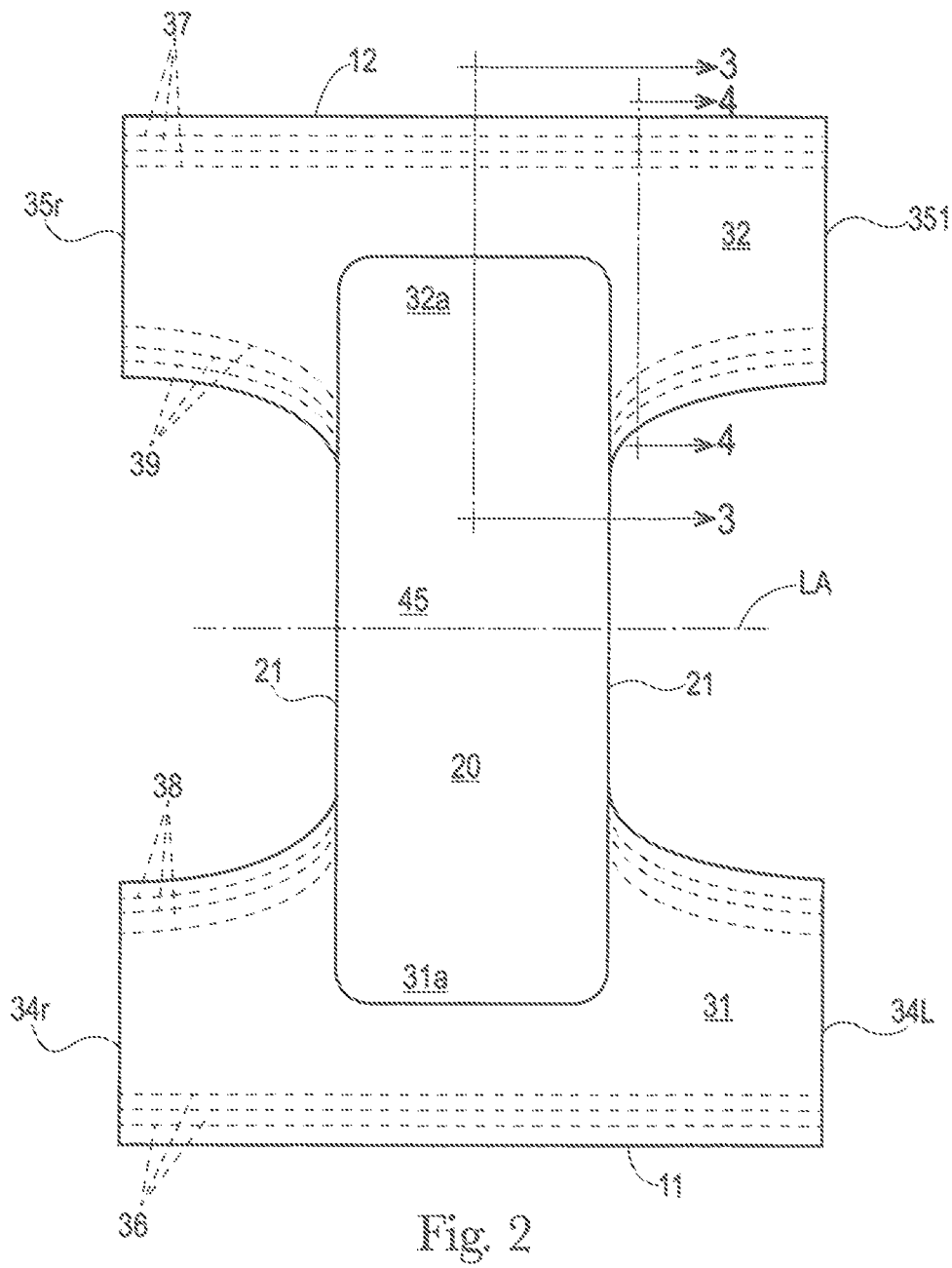
FIG. 2 is a simplified plan view of a precursor structure of a disposable absorbent pant, shown with inner or wearer-facing surfaces upward.

FIG. 2 is a simplified plan view of the precursor structure of the pant 10 shown in FIG. 1, shown prior to joining of front and rear portions 31, 32 along their respective side edges 34l, 35l and 34r, 35r. Front region 31a, including front portion 31, and rear region 32a, including rear portion 32, may each include anywhere from 25 percent to 40 percent of the overall longitudinal length of the precursor structure; correspondingly, a crotch region 45 may include anywhere from 20 percent to 50 percent of the overall longitudinal length of the precursor structure, with at least a portion thereof lying at lateral axis LA. To form pant 10, the precursor structure may be folded along lateral axis LA to bring front and rear regions 31a, 32a, and front and rear portions 31, 32 together such that their side edges 34l, 35l and 34r, 35r, respectively, may be joined at seams 33l, 33r (as shown in FIG. 1). Seams 33l, 33R may be formed by adhesive, thermal, pressure, or ultrasonic bonding, and combinations thereof. In an alternative example, the seams may be formed by mechanical fasteners such as cooperating pairs of hook-and-loop fastening components disposed along side edges 34r, 35r and 34l, 35l. Fasteners may also include tape tabs, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428, 526.

Still referring to FIG. 2, one or both of front and rear portions 31, 32 may include at least a first elastic member 36, 37 disposed nearer the waist edges 11, 12 and at least a second elastic member 38, 39, disposed nearer the leg opening edges 13l, 13r. As suggested in FIG. 2, one or a plurality of waist elastic members 36, 37 may be disposed in a substantially straight lateral orientation, and one or a plurality of leg elastic members 38, 39 may be disposed along curvilinear paths to provide hoopwise elastic stretch about the leg openings 13l, 13r (as shown in FIG. 1). For purposes of manufacturing a pant having a neat appearance as will be described below, it may be desired that leg elastic members 38, 39 terminate proximate the respective longitudinal edges 21 of chassis 20. For purposes herein, where used to describe a positional relationship between two features, "proximate" is intended to mean within 2.0 cm, more preferably within 1.0 cm, of the identified features.

Elastic members 36, 37, 38 and 39 may be in the form of film or sections thereof, strips, ribbons, bands or strands of circular or any other cross-section, formed in any configuration of any elastomeric material such as described in, for example, co-pending U.S. application Ser. Nos. 11/478,386 and 13/331,695, and U.S. Pat. No. 6,626,879. A suitable example is LYCRA HYFIT strands, a product of Invista, Wichita, Kans.

Figure 3A:
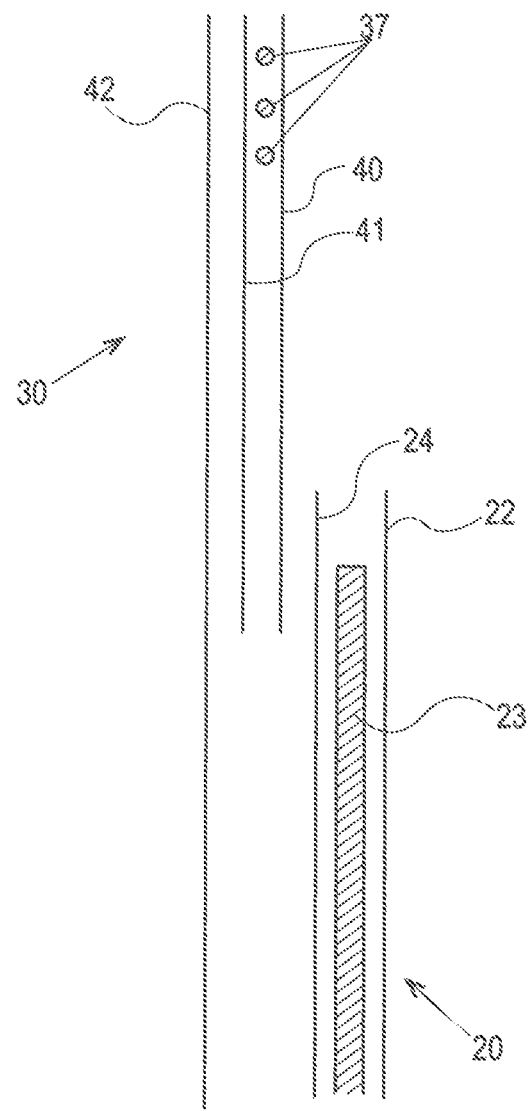
FIGS. 3A-3C are varying longitudinal cross-section views taken at line 3-3 of FIG. 2.
Figure 3B:
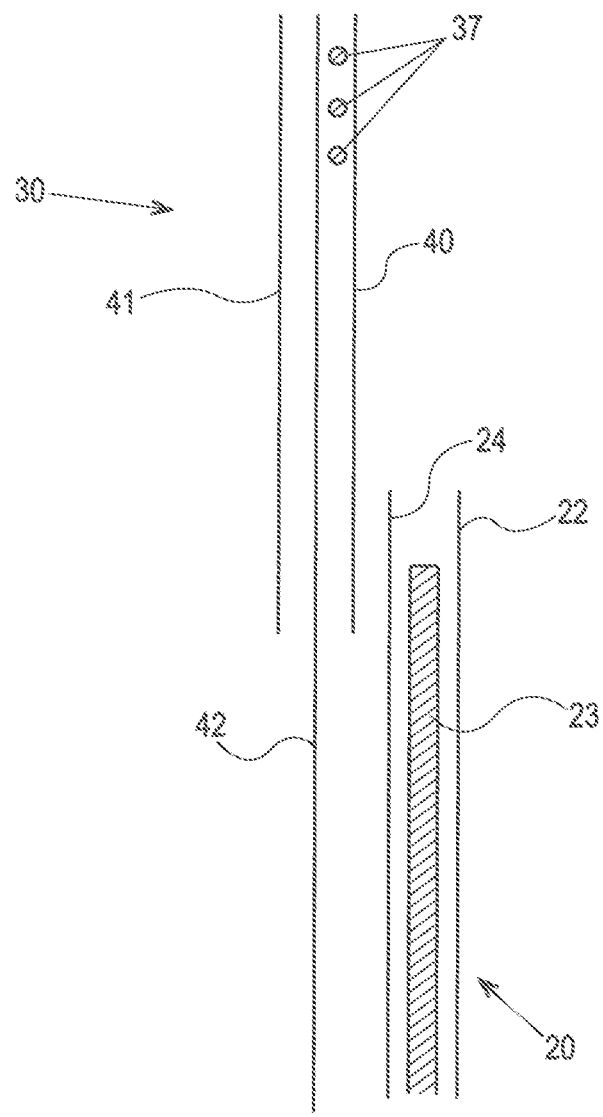
Figure 3C:
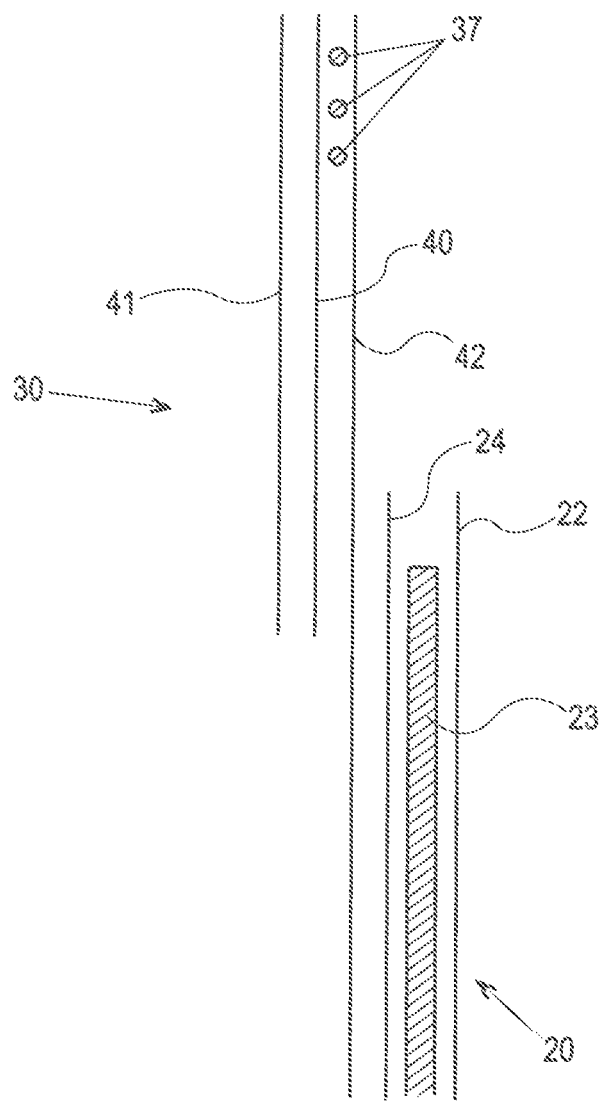

FIGS. 3A-3C are examples of potential longitudinal cross-sections taken at line 3-3 through the rear portion 32 of the belt structure and rear region of the pant as shown in FIG. 2, depicting features in three possible configurations. It can be appreciated that in each of these particular examples, the cross-section may substantially mirror a cross-section taken through the front portion 31 of the belt structure and the front region of the pant.

Figure 4:
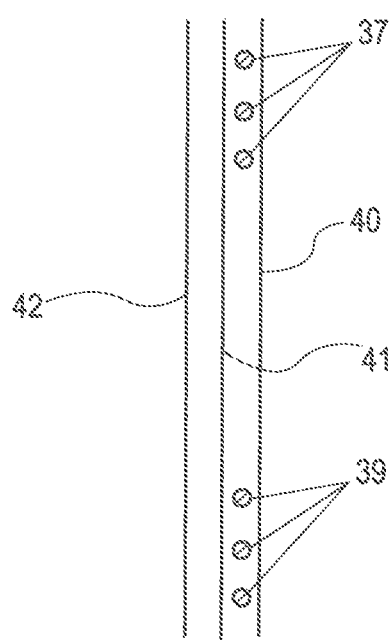
FIG. 4 is a longitudinal cross-section view taken at line 4-4 of FIG. 2.

FIG. 4 is an example of a potential longitudinal cross-section taken at line 4-4 through the rear portion 32 of the belt structure and rear region of the pant as shown in FIG. 2, depicting features in one configuration. It can be appreciated that this cross-section may also be a substantial mirror image of a cross-section taken through the front portion 31 of the belt structure and the front region of the pant. Belt structure 30 where shown in FIG. 4 has the same layers and components as those depicted in FIG. 3A, but with the addition of leg elastic members 39 and without the chassis components, as a result of the location of the cross-section. As suggested in FIG. 2, leg elastic members 39 may terminate proximate the longitudinal edges 21 of central chassis 20; thus, they do not appear in FIGS. 3A and 3B. Additional elastics (not shown) may be disposed longitudinally between the waist elastics and the leg elastics.

Referring to FIGS. 3A-3C, chassis 20 may have liquid permeable topsheet 22 forming at least a portion of its inner, wearer-facing surface. Topsheet 22 may be formed of a nonwoven web material which is preferably soft and compatible with sensitive skin, and may be formed of and have any of the features of topsheets used in disposable diapers, training pants and inserts including those described in, for example, U.S. application Ser. No. 12/841,553. Chassis 20 may also have an outward-facing backsheet 24, which may be liquid impermeable. Backsheet 24 may be formed of and have any of the features of backsheets used in disposable diapers and training pants including those described in, for example, the U.S. patent application referenced immediately above. Chassis 20 may also have an absorbent core 23 disposed between topsheet 22 and backsheet 24. Absorbent core 23 may include one or more absorbent acquisition, distribution and storage material layers and/or components; it may be formed of and have any of the features of absorbent cores used in disposable diapers and training pants including those described in, for example, the U.S. patent application referenced immediately above.

As suggested in FIGS. 3A-3C, chassis 20 may be affixed to a belt structure 30, to the inner, wearer-facing side thereof, or alternatively, to the outer, garment-facing surface thereof. Chassis 20 may be bonded to the belt structure 30 by adhesive, by thermal bonds/welds, mechanical fasteners or a combination thereof.

Referring to FIGS. 3A and 4, belt structure 30 may have a first belt layer 40, which may be formed of a suitable nonwoven web material. Since the first belt layer may come into direct contact with the wearer's skin, it may be deemed preferable to select a nonwoven web material for the layer that is soft, comfortable and relatively breathable/vapor permeable. One or more waist elastic members 37 may be disposed between first belt layer 40 and a second belt layer 41. Second belt layer 41 may be formed of the same, similar or differing nonwoven web material as first belt layer 40. First belt layer 40 and second belt layer 41 may be bonded together by adhesive, a pattern of thermal bonds or a combination thereof, such that first belt layer 40 and second belt layer 41 form a laminate, with the one or more waist elastic members 37 sandwiched and affixed there between. Similarly, referring to FIG. 4, the one or more leg elastic members 39 may be affixed and sandwiched between first belt layer 40 and second belt layer 41.

Also as shown in FIGS. 3A-3C and 4, the belt structure may include a longitudinally extending wrapping layer 42. Wrapping layer 42 may form a layer that wraps not only about the front and rear portions of the belt structure, but also extends from the front portion, around and beneath the chassis 20 through the crotch region, and into the rear portion. The wrapping layer 42 may be formed of a single material web disposed as a layer of the rear portion 32 of the belt structure 30, the central chassis 20, and the front portion 31 of the belt structure 30. Wrapping layer 42 may be disposed so as to form an outer layer or outer cover of the belt structure 30 in the front and rear portions as suggested in FIGS. 3A and 4, an intermediate layer in the front and rear portions as suggested in FIG. 3B, or an inner layer as suggested in FIG. 3C. Wrapping layer 42 may be formed of any suitable nonwoven web material having desired properties of softness and mechanical strength. Wrapping layer 42 is optional. That is, there are embodiments in which there is no wrapping layer and the rear portion 32 of the belt and the front portion 31 of the belt, when the article is laid out flat, may be discrete and without a common layer. The only part connecting the two belts in such embodiments would be the center chassis.

Examples of suitable nonwoven web materials useful for forming any of layers 40, 41 and 42 are described in U.S. application Ser. No. 13/090,761. Some examples described above, as well as other examples not expressly described, may also be advantageous because they may lend themselves to relatively efficient manufacture.

In general terms, the belt structure comprises an inner layer that is in contact with the wearer's skin when the article is worn. This inner layer may be formed of an inner nonwoven web comprising an inner surface. According to different embodiments described above, the inner surface that is in contact with the wearer's skin may be the first belt layer (for example, see FIG. 3A) or may be the wrapping layer (for example, see FIG. 3C). The belt structure also comprises an outer layer formed of an outer nonwoven web comprising an outer surface. This outer surface is the outermost surface of the article. In some embodiments described above, the outer surface may be the wrapping layer (for example, see FIG. 3A) or may be the second belt layer (for example, see FIG. 3C). In some embodiments, the inner surface of the belt comprises a treatment, and the inner surface is then different than the outer surface. The outer surface may itself have a treatment, but in some embodiments, the outer surface treatment will be different than the inner surface treatment.

The treatment for a surface, such as an inner surface or an outer surface, may be selected from the group consisting of application of a personal care composition such as a lotion or surfactant, texturing, aperturing, and combinations thereof.

Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392 to Land, the disclosure of which is incorporated by reference herein. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. No. 6,645,569 to Cramer et al.; U.S. Pat. No. 6,863,933 to Cramer et al.; and U.S. Pat. No. 7,112,621 to Rohrbaugh et al.; and in U.S. patent application Ser. Nos. 10/338,603 and 10/338,610 by Cramer et al.; and Ser. No. 13/005,237 by Lu et al.

The individual fibers may be monocomponent or multi-component. The multicomponent fibers may be bicomponent, such as in a core-and-sheath or side-by-side arrangement. Often, the individual components comprise polyolefins such as polypropylene or polyethylene, or their copolymers, polyesters, thermoplastic polysaccharides or other biopolymers.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance softness perceptions of the laminate, nonwovens may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921.

Other examples of nonwoven web that may be useful in the present laminate may be an SMS web (spunbond-meltblown-spunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXF0YYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web.

A nonwoven web useful as a component to form one or any layer may be pre-bonded, prior to aperturing as described below. A batt of fibers may be calendered and pre-bonded in a pattern, to consolidate the batt/fibers and create a pattern of bonds that adds tensile strength and dimensional stability, converting the batt of fibers to a coherent and useable nonwoven web material. The web may be imparted with a pattern of pre-bonding as described in, for example, U.S. Pat. No. 5,916,661 (pre-bonding in a pattern of "point calendered bonds 200 to form a coherent web structure") and U.S. application Ser. No. 13/893,405 (pattern of "primary fiber bonds"). The pre-bonding may consist of a pattern of thermal bonds, mechanical bonds or adhesive bonds, although in some circumstances thermal bonding may be preferred.

Layers of nonwoven web may sandwich one or more elastic members such as a plurality of strands of an elastomeric material, such as an elastane (for example, LYCRA HYFIT fiber, a product of Invista, Wichita, Kans.). Layers of nonwoven web may be joined together about elastic strands by adhesive deposited between the layers, by thermal bonds, by compression bonds, or by a combination thereof. In other examples, the one or more elastic members may be strips or a section of film formed of elastomeric material.

The elastomeric members can also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments). The elastomeric members can have a decitex ranging from 50 to 2000, or any integer value for any decitex value in this range, or any range formed by any of these integer values. The elastomeric members may be in a form of film. Examples of films have been described extensively in prior patent applications (see, for example, U.S. Pat. App. Pub. No. 2010/0040826). The film may be created with a variety of resins combined in at least one of several sublayers, the latter providing different benefits to the film.

During manufacture of the belt structure, the elastic member such as elastic strands may be strained lengthwise by a desired amount as they are being incorporated into the belt structure. Upon subsequent relaxation of the belt, the elastic member such as elastic strands will contract toward their unstrained lengths. This causes the layers of nonwoven material to gather and form ruffles or rugosities having ridges and valleys generally transverse to the lengths of the elastic strands. The term "rugosity" or "rugosities" as used herein may mean ridges, wrinkles, and/or creases formed in a substrate proximate to elastic elements attached to or otherwise engaged with the substrate when the elastic elements are in a relaxed state or a partially relaxed state. Each rugosity has a minimum amplitude of 0.25 mm.

It may be appreciated that the size(s) and shape(s) of the rugosities will be affected, and may be manipulated, by design of the pattern of joined portions and/or bonding between the layers of nonwoven web, with respect to each other and with respect to elastic strands. When joining and/or bonding is effected using adhesive deposited upon one or both layers prior to lamination, the adhesive may be deposited in a pattern. Examples of methods for applying patterned deposits of adhesive to a nonwoven web substrate to enable manufacture of an elasticized laminate are described in U.S. Pat. No. 8,186,296. The pattern selected may be effected by design of a correspondingly designed roller. The pattern of adhesive to be applied may be designed to affect the size(s) and shape(s) of the rugosities. The layers may be adhesively joined and/or bonded to each other at the locations of adhesive deposits, and remain unjoined or unbonded, or free, of each other at other locations, such that they may move and shift slightly relative each other as the laminate is moved and stretched, as during wear of the article. Similarly, when joining and/or bonding is effected using thermal calender bonding, the joining and/or bonding pattern may be designed to affect the size(s) and shapes of the rugosities.

Personal Care Composition

In some embodiments, the inner surface of the belt may be treated with a personal care composition. The personal care compositions of the present invention may be fluid or pasty at processing temperature upon application to the surface, depending on the application method of the personal care composition to the surface. The personal care composition comprises components which have affinity to the surface, which may be a nonwoven substrate, and may partially migrate into the substrate. The personal care composition is selected so as not to inhibit the functionality of the waist belt, as discussed in the further detail below. When applied to the inner surface of the belt, the personal care composition may impart softness to the wearer, and also provide therapeutic or protective coating benefits to the wearer's skin. The composition may be transferable to the wearer's skin by normal contact, wearer motion, and/or body heat. The inner surface of the belt may be treated with an effective amount of the personal care composition, an effective amount depending on the particular composition used.

Examples of personal care compositions useful herein are disclosed in U.S. Pat. No. 6,533,765.

In some embodiments, the personal care composition may be in the form of an oil-in-water emulsion. By oil-in-water emulsion from, what is meant is an emulsion having water as the continuous phase. Water content of oil-in-water emulsions useful herein are from 50% to 99%, or from 60% to 95%, or from 85% to 90%.

Oil-in-water emulsions are useful in that they have less tendency of migrating into the surface and even into adhesive compositions for adhering the elastic members on the waist belt nonwoven. Contact of oleaginous components with the adhesive compositions may plasticize the adhesive composition, causing a modulus reduction or loss of cohesive strength. Such deterioration of the adhesive composition may result in loss of contractive force of the elastic members attached therewith, or ultimately separation of the elastic members from the waist belt nonwoven materials.

Oil-in-water emulsions are useful in that they may reduce the coefficient of friction of any type of nonwoven. As such, even nonwoven of lower basis weight or those without softness imparting additives may be imparted softness. For example, emulsions may impart softness to nonwovens that have a basis weight of no more than 25 gsm, or no more than 20 gsm, or no more than 17 gsm. Emulsions may impart softness to nonwovens that are made of propylene homopolymer. Emulsions may impart softness to nonwovens that are not apertured or not textured. Emulsions may impart softness to nonwovens made by spunbond.

Emulsions may further be applied to other elements of the absorbent article for imparting softness, such as the inner or outer cuffs, topsheet, outer cover, or outer surface of the outer layer of the belt, for example, the backsheet if there is no outer cover or wrapping layer. The absorbent article of the present invention may have a pair of opposing cuffs along the longitudinal edges of the central chassis. Inner and outer cuffs may be provided. Cuffs may include elastics encased along the longitudinal direction for good fit of the absorbent article. The emulsion of the present invention may be applied with less impact to the elastics encased in the cuffs. The absorbent article of the present invention may have an outer cover on the garment facing side of the central chassis, the outer cover comprising nonwoven material. Application of the emulsion on the outer cover or outer surface of the belt may reduce the papery noise of the absorbent article caused by friction of the hands and the outer cover, and connote a soft and high quality perception of the absorbent article as a whole. A papery noise may be associated with harshness to skin, or low quality material. When the emulsion is applied to the outer layer, the inner layer may be treated in a different way, or may be treated with an emulsion having different skin care benefit.

Oil-in-water emulsions are useful in that the viscosity may be adjusted for various application forms to the nonwoven on-line. Application forms include, but are not limited to, contact coating, spray coating, and ink jet printing. The oil-in-water emulsions useful herein may have a viscosity of 1 to 100,000 mPas.

The personal care composition of the present invention may comprise a cationic surfactant. Cationic surfactants are useful for providing oil-in-water emulsions, and may also contribute in prevention of microbial growth on the product or the package for the product. This is particular beneficial for compositions that contain a high percentage of water. Cationic surfactants useful herein include the following. Suitable levels of the cationic surfactant herein are in the range of from 0.001% to 20%, or from 1% to 10%, or from 5% to 10%, by weight of the composition.

A first preferred type of cationic surfactant comprises, as the principal active, compounds of the formula $$\{R_{4-m}-N^{+}-[(CH_2)_n-Y-R^1]_m\}X^- \qquad (1)$$

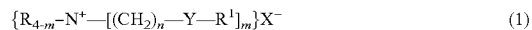

wherein each R substituent is either hydrogen, a short chain $C_1$-$C_6$, preferably $C_1$-$C_3$ alkyl or hydroxyalkyl group, e.g., methyl, ethyl, propyl, hydroxyethyl, and the like, poly ($C_{2-3}$ alkoxy), preferably polyethoxy, benzyl, or mixtures thereof; each m is 2 or 3; each n is from 1 to about 4, preferably 2; each Y is —O—(O)C—, —C(O)—O—, —NR—C(O)—, or —C(O)—NR—; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group, and $X^-$ can be any softener-compatible anion, preferably, chloride, bromide, methylsulfate, ethylsulfate, sulfate, and nitrate, more preferably chloride or methyl sulfate;

A second type of preferred cationic surfactant has the general formula:

$$[R_3N^+CH_2CH(YR^1)(CH_2YR^1)]X^-$$

wherein each Y, R, $R^1$, and $X^-$ have the same meanings as before. Such compounds include those having the formula:

$$[CH_3]_3N^{(+)}[CH_2CH(CH_2O(O)CR^1)O(O)CR^1]Cl^{(-)} \qquad (2)$$

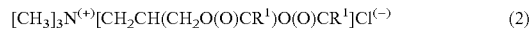

wherein each R is a methyl or ethyl group and preferably each $R^1$ is in the range of $C_{15}$ to $C_{19}$. As used herein, when the diester is specified, it can include the monoester that is present.

These types of agents and general methods of making them are disclosed in U.S. Pat. No. 4,137,180, Naik et al., issued Jan. 30, 1979, which is incorporated herein by reference. An example of a preferred DEQA (2) is the "propyl" ester quaternary ammonium fabric cationic surfactant having the formula 1,2-di(acyloxy)-3-trimethylammoniopropane chloride.

A third type of preferred cationic surfactant has the formula:

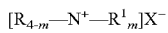  (3)

wherein each R, R$^1$, and X$^-$ have the same meanings as before.

A fourth type of preferred cationic surfactant has the formula:

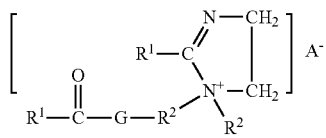  (4)

wherein each R, R$^1$, and A$^-$ have the definitions given above; each R$^2$ is a C$_{1-6}$ alkylene group, preferably an ethylene group; and G is an oxygen atom or an —NR— group;

A fifth type of preferred cationic surfactant has the formula:

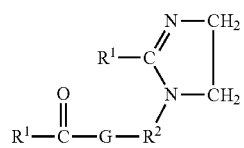  (5)

wherein R$^1$, R$^2$ and G are defined as above.

A sixth type of preferred cationic surfactant are condensation reaction products of fatty acids with dialkylenetriamines in, e.g., a molecular ratio of about 2:1, said reaction products containing compounds of the formula:

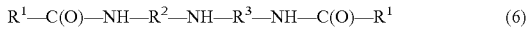  (6)

wherein R$^1$, R$^2$ are defined as above, and each R$^3$ is a C$_{1-6}$ alkylene group, preferably an ethylene group and wherein the reaction products may optionally be quaternized by the additional of an alkylating agent such as dimethyl sulfate. Such quaternized reaction products are described in additional detail in U.S. Pat. No. 5,296,622, issued Mar. 22, 1994 to Uphues et al., which is incorporated herein by reference;

A seventh type of preferred cationic surfactant has the formula:

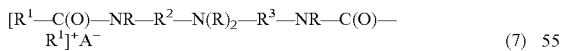  (7)

wherein R, R$^1$, R$^2$, R$^3$ and A$^-$ are defined as above;

An eighth type of preferred cationic surfactant are reaction products of fatty acid with hydroxyalkylalkylenediamines in a molecular ratio of about 2:1, said reaction products containing compounds of the formula:

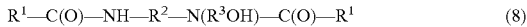  (8)

wherein R$^1$, R$^2$ and R$^3$ are defined as above;

A ninth type of preferred cationic surfactant has the formula:

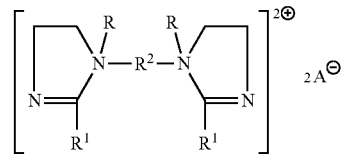  (9)

wherein R, R$^1$, R$^2$, and A$^-$ are defined as above.

Non-limiting examples of compound (1) are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate.

Non-limiting examples of compound (2) is 1,2 di(stearoyl-oxy) 3 trimethyl ammoniumpropane chloride.

Non-limiting examples of Compound (3) are dialkylenedimethylammonium salts such as dicanoladimethylammonium chloride, di(hard)tallowdimethylammonium chloride dicanoladimethylammonium methylsulfate. An example of commercially available dialkylenedimethylammonium salts usable in the present invention is dioleyldimethylammonium chloride available from Witco Corporation under the trade name Adogen® 472 and dihardtallow dimethylammonium chloride available from Akzo Nobel Arquad 2HT75.

A non-limiting example of Compound (4) is 1-methyl-1-stearoylamidoethyl-2-stearoylimidazolinium methylsulfate wherein R$^1$ is an acyclic aliphatic C$_{15}$-C$_{17}$ hydrocarbon group, R$^2$ is an ethylene group, G is a NH group, R$^5$ is a methyl group and A$^-$ is a methyl sulfate anion, available commercially from the Witco Corporation under the trade name Varisoft®.

A non-limiting example of Compound (5) is 1-tallowylamidoethyl-2-tallowylimidazoline wherein R$^1$ is an acyclic aliphatic C$_{15}$-C$_{17}$ hydrocarbon group, R$^2$ is an ethylene group, and G is a NH group.

A non-limiting example of Compound (6) is the reaction products of fatty acids with diethylenetriamine in a molecular ratio of about 2:1, said reaction product mixture containing N,N"-dialkyldiethylenetriamine with the formula:

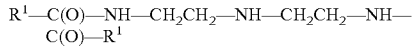

wherein R$^1$—C(O) is an alkyl group of a commercially available fatty acid derived from a vegetable or animal source, such as Emersol® 223LL or Emersol® 7021, available from Henkel Corporation, and R$^2$ and R$^3$ are divalent ethylene groups.

A non-limiting example of Compound (7) is a difatty amidoamine based softener having the formula:

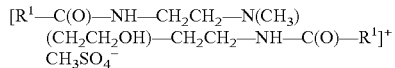

wherein R$^1$—C(O) is an alkyl group, available commercially from the Witco Corporation e.g. under the trade name Varisoft® 222LT.

An example of Compound (8) is the reaction products of fatty acids with N-2-hydroxyethylethylenediamine in a molecular ratio of about 2:1, said reaction product mixture containing a compound of the formula:

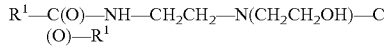

wherein R$^1$—C(O) is an alkyl group of a commercially available fatty acid derived from a vegetable or animal source, such as Emersol® 223LL or Emersol® 7021, available from Henkel Corporation.

An example of Compound (9) is the diquaternary compound having the formula:

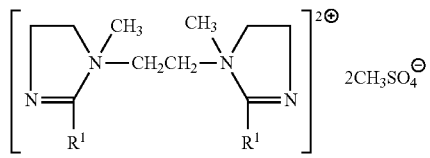

wherein $R^1$ is derived from fatty acid, and the compound is available from Witco Company.

It will be understood that combinations of cationic surfactants disclosed above are suitable for use in this invention.

In the cationic nitrogenous salts hereinabove, the anion $A^-$, which is any surfactant compatible anion, provides electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. Chloride and methylsulfate are preferred herein as anion A. The anion can also, but less preferably, carry a double charge in which case $A^-$ represents half a group.

The personal care composition of the present invention may comprise a thickener that renders desired viscosity to the composition. Suitable levels of the thickener herein are in the range of from 0.001% to 10%, or from 0.01% to 5%, or from 0.5% to 2%, by weight of the emulsion composition.

In one embodiment, the thickener suitable for use herein can be selected from thickening stabilizers. These include gums and other similar polysaccharides, for example gellan gum, carrageenan gum, xanthan gum, Diutan gum (available from CP Kelco), and other known types of thickeners and rheological additives such as Rheovis® CDP (available from BASF), Alcogum® L-520 (available from Alco Chemical), and Sepigel 305 (available from SEPPIC).

In another embodiment, cationic acrylic-based polymers are utilized as the thickener herein. One example of such thickener is poly(acrylic acid) available under the tradename Carbomer. Another example is cationic acrylic based polymer, sold under the name Rheovis® CDE by BASF.

As mentioned above, the suitable viscosity of the personal care composition herein depends on the form in which it is applied to a surface. For applying the composition by contact coating, the composition suitably has a relatively high viscosity and low water content. Contact coating is useful for controlling the application in cross machine direction, and also for keeping the water level low in order to prevent machine contamination and minimizing microbial growth. For applying the composition by spray coating and ink jet printing, the composition suitably has a relatively low viscosity and high water content. Spray coating is useful for providing the treatment economically. Ink jet printing is useful for providing precision application to the surface in both machine direction and cross machine direction, as well as patterning and altering the amount in certain areas. For example, the composition may be applied only to areas which have higher contact or friction with the wearer's skin. One suitable embodiment for ink jet printing in high efficiency production of hygienic articles is disclosed U.S. Pat. No. 6,811,239, herein incorporated by reference.

Regardless of the application method of the composition, the amount of application per surface may be from 0.1% to 20%, or from 1% to 10%, or from 2% to 10% by weight of the cationic surfactant to the weight of the surface substrate.

The personal care composition may further contain additional components for providing aesthetic or functional benefit to the composition or skin, such as sensory benefits relating to appearance, smell, or feel, therapeutic benefits, or prophylactic benefits, as well as biocides and preservatives. When included, the composition comprises no more than about 20%, or about 10% of additional components.

Additional components useful herein include; skin care actives such as chamomile extract, aloe extract, green tea extract, tocopherol, proteins, vitamins such as vitamin A and vitamin E; perfumes; and preservatives such as methyl paraben, ethyl paraben, and phenoxy ethanol. Preservatives are useful for controlling the microbial growth of the residual water from the emulsion in the absorbent article.

Nonionic surfactants, silicones, hydrocarbon waxes, and other emollients may be included in the composition to the extent they are stabilized by the surfactants, and in the oil-in-water emulsion form. As described above, components of oleaginous nature are kept to an amount such that migration of these components to the adhesive composition of the belt is prevented.

In other embodiments, the personal care compositions may comprise: (1) an emollient(s); (2) an immobilizing agent(s) for the emollient; (3) optionally a hydrophilic surfactant(s); and (4) other optional components, such as those described in U.S. Pat. No. 5,635,191. Additional personal care compositions that may be beneficial for skin may typically include at least one active ingredient for the treatment or prevention of skin ailments like diaper rash or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, and colloidal oatmeal, and combinations of these. Examples of skin care compositions are disclosed in U.S. Pat. No. 8,466,355.

Aperturing/Texturing

In some embodiments, at least one of the inner and outer surfaces of the belt may be treated with aperturing. Examples of suitable aperturing may be found in Ser. No. 14/032,595. Creating apertures in nonwoven material used to form, for example, a topsheet, may enhance its ability to allow aqueous liquid exudates to pass therethrough. In some circumstances this may be desired because materials of which topsheets are often formed may include polymers (such as polyolefins) that are normally hydrophobic, and pores or passageways ordinarily present between the nonwoven fibers may be insufficiently large to allow aqueous liquids to pass therethrough at a desired rate because the material tends to repel aqueous liquid.

An example of a process for creating apertures in a pre-bonded nonwoven web to be used to form a topsheet is described in U.S. Pat. Nos. 5,916,661 and 5,629,097. This process involves rolling the pre-bonded nonwoven web through the nip between a pair of rollers, one of which bears a pattern of raised bonding protrusions, and supplying heating energy to heat the fibers beneath the protrusions in the nip. When appropriately controlled pressure and heating energy are provided at the nip, a pattern of suitable bonds or "weakened, melt-stabilized locations" having rod shapes or other shapes results. At the bond sites, the polymer fibers of the web are melted, compressed and thereby fused, such that the fused polymer material at the bond sites is relatively thin (in the z-direction) and frangible. Upon subsequent cross direction incremental stretching of the bonded nonwoven web as described in the above-cited patents, the material at the bond sites or "melt-stabilized locations" breaks and apertures open in a direction transverse to the long dimension of the rod shapes.

In comparison to a process in which apertures are simply punched or cut through the web without application of heating energy, the bonding/stretching process described in the above-cited patent does not cut the fibers, which can result in loose fibers and fraying about the edges of the punched or cut apertures. In contrast, the bonding/stretching process described herein tends not to create loose fibers, and provides more neatly defined edges about the apertures. Following incremental stretching, the web may be allowed to relax, which may cause the apertures to close to some extent, but they will still be present.

In another example, the web may be bonded by compression bonding without the application of externally-produced or additional heating energy. Examples of suitable compression bonding systems utilizing rollers are described in, for example, U.S. Pat. Nos. 4,854,984 and 4,919,738. In these types of mechanisms, a first roller and second roller are arranged with their axes in parallel and urged together to form a nip. The first roller may have on its surface one or more bonding protrusions arranged in a pattern. The first roller and second roller may be urged together by one or more actuators such as bellows-type pneumatic actuators acting directly or indirectly on one or both of their axles, to provide and regulate compression, beneath the protrusions at the nip, of the web material as it passes therethrough, in the manner described in the aforementioned patents. A compression bonding mechanism such as, but not limited to, the mechanism described in the aforementioned patents, provides bonding of a nonwoven web material through rapid compression of superimposed fibers beneath the bonding protrusions, along the roller nip line. Without intending to be bound by theory, it is believed that rapid compression beneath the protrusions causes the respective materials to be rapidly deformed and partially expressed together from beneath the protrusions, to form structures of deformed, compressed and entangled fiber material beneath and/or around the protrusions. Welds or weld-like structures at or about the protrusions result. In some circumstances compression bonding provides advantages, including relative simplicity and cost effectiveness. It may reduce or eliminate the need for more complex bonding systems that require a system to supply externally produced or additional heating energy. Without intending to be bound by theory, it is believed that these advantages are substantially independent of variations in line speeds in at least some circumstances, including line speeds within currently known economically and technically feasible ranges for manufacture of disposable diapers and training pants. Following such creation of compression bonds, the web may be incrementally stretched to create apertures at the bond sites, in the manner taught by U.S. Pat. No. 5,916,661.

As noted, as suggested in U.S. Pat. No. 5,916,661, prior to aperturing, the nonwoven web may be pre-bonded with a relatively dense pattern of thermal/calender bonds. Following that, a pattern of apertures may simply be punched or cut through the web. A relatively dense pattern of bonding can serve to minimize loose cut fibers and fraying, and help maintain defined edges of apertures formed by cutting or punching.

It will be appreciated that the apertures created need not necessarily be rod-shaped. The apertures may be rod-shaped, arc-shaped, other curved finite paths, circular, oval, elliptical or polygon, and any combinations thereof. It may be desired in some circumstances, however, that the longest dimension of a majority of the individual apertures be oriented along the machine direction of the nonwoven web—particularly when the web or components of it are formed by processes that produce a machine direction bias in the fibers such as spunbonding or spunlaying processes.

It will also be appreciated that the apertures may be arranged in varying patterns, such as but not limited evenly-spaced and aligned rows and columns, offset rows and columns, diagonal patterns, shaped patterns, etc. Additionally, the pattern of the apertures may be substantially similar or identical to the pattern of the pre-bonds (if present), in one or more of machine-direction spacing, cross-direction spacing, aperture shape and aperture size. Using respective patterns of pre-bonds and apertures that are substantially similar in one or more respects noted can help give the material a more uniform, orderly and/or coherent appearance, and may also help enhance tensile strength as compared with a web in which respective patterns of pre-bonds and apertures do not have such similarities.

Using a nonwoven web that has been apertured in the manner described above to form one of the nonwoven web layers in a belt as described above can provide attractive and interesting effects. The apertures and the material surrounding them may interact with the contraction-induced rugosities in the web layer as the belt is moved and stretched as, for example, during wear. Apertures in a layer will open, close, change shape and shift relative the other layer, providing a visual impression of complexity, depth and added texture. Apertures with various shapes, and angles relative the machine direction, can result in z-direction projections and/or ridges along the edges of the apertures when the belt structure contracts.

When the belt structure contracts in either the lateral or longitudinal direction, "flaps" created by the aperture shapes may stand up and add z-direction loft in addition to the height of the rugosities. The added loft may contribute to tactile and visual perceptions of added softness and/or breathability. Additionally, with expansion and contraction of the belt structure the "flaps" may open and close, alternately revealing and concealing any contrasting appearance and/or color of the underlying layer, and giving the belt structure a more complex and lively appearance. It may be appreciated that the pattern of apertures selected may be coordinated with the pattern of adhesive selected to adhere the laminate, for varying effects.

In some embodiments, at least one of the inner and outer surfaces of the elastomeric belt may be treated with texturing. In some embodiments, both inner and outer surfaces of the belt may be treated with texturing, but with different texturing for different purposes. For example, different texturing for the inner and outer surfaces respectively may result in differing coefficients of friction for the inner and outer surfaces. For example, texturing may provide a desirably high coefficient of friction on an inner surface to help the article stay in place on the wearer. The inner surface may then also be treated with a personal care composition for softness. The same article then may then have an outer surface treated differently, or not treated at all.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front waist region, a rear waist region, and a crotch region, and comprising:
    a central chassis occupying the crotch region and comprising left and right longitudinal edges; a liquid permeable topsheet; a backsheet, and an absorbent core disposed between the topsheet and the backsheet;
    a belt structure disposed about the central chassis, the belt structure comprising an elasticized multilayer web overlaying the backsheet to the outside thereof in the front and rear waist regions, the belt structure extending laterally and longitudinally outward from the chassis and laterally from each of the left and right longitudinal edges in each of the front and rear waist regions, the belt structure having a front portion having a front waist edge, front left and right leg opening edges, and front left and right side edges, and the belt structure having a rear portion having a rear waist edge, rear left and right leg opening edges, and rear left and right side edges, the respective front and rear left side edges and the respective front and rear right side edges being joined at side seams, the belt structure forming a waist opening and left and right leg openings, wherein each of the front and rear portions of the belt structure further comprises:
    an inner layer formed of an inner nonwoven web comprising an inner surface;
    an outer layer formed of an outer nonwoven web comprising an outer surface;
    a plurality of leg elastic members disposed along curvilinear paths;
    wherein the inner nonwoven web has a higher basis weight than the outer nonwoven web;
    wherein the inner surface of the belt comprises a treatment and wherein the inner surface is different than the outer surface; and
    wherein the treatment is application of a personal care composition.

2. The absorbent article of claim 1, wherein the personal care composition is an oil-in-water emulsion comprising a cationic surfactant.

3. The absorbent article of claim 2, wherein the amount of application per surface is from 2% to 10% by weight of the cationic surfactant to the weight of the surface substrate.

4. The absorbent article of claim 1, wherein the personal care composition further comprises a thickener and a preservative.

5. The absorbent article of claim 1, wherein the personal care composition further comprises a skin care active selected from the group consisting of chamomile extract, aloe extract, green tea extract, tocopherol, proteins, and vitamins.

6. The absorbent article of claim 1, wherein the personal care composition is applied to the inner surface by an application method selected from the group consisting of contact coating, spray coating, and ink jet printing.

7. The absorbent article of claim 1, wherein the personal care composition is applied to a surface of the inner belt formed by a nonwoven which is a propylene homopolymer of no more than about 25 gsm.

8. The absorbent article of claim 1, the absorbent article further comprising a pair of opposing cuffs along the longitudinal edges of the central chassis, wherein the personal care composition is further applied to the cuffs.

9. The absorbent article of claim 1, the absorbent article further comprising an outer cover on the garment facing side of the central chassis, the outer cover comprising nonwoven material, wherein the personal care composition is further applied to the outer cover.

10. The absorbent article of claim 1, wherein the personal care composition is applied to the inner surface in a pattern.

11. The absorbent article of claim 1, wherein the inner surface of the belt has a higher coefficient of friction than the outer surface of the elastomeric belt.

12. The absorbent article of claim 1, wherein the inner surface of the belt has a different texture than the outer surface of the belt.

13. The absorbent article of claim 1, wherein the outer surface of the belt has at least about two times the number of rugosities than the inner surface of the belt.

14. The absorbent article of claim 1, wherein the inner surface of the belt in the front region comprises a different treatment than the inner surface of the belt in the rear region.

15. The absorbent article of claim 1, wherein at least one of the outer surface of the belt and the inner surface of the belt comprises apertures.

16. The absorbent article of claim 15, wherein the apertures are oriented substantially parallel to a latitudinal centerline.

17. The absorbent article of claim 1, wherein both the outer surface of the belt and the inner surface of the belt comprise apertures, and wherein the inner surface apertures are different than the outer surface apertures.

* * * * *